US009008975B2

(12) United States Patent
Koshihara et al.

(10) Patent No.: US 9,008,975 B2
(45) Date of Patent: Apr. 14, 2015

(54) APPARATUS FOR DETECTING PERIODIC DEFECT AND METHOD THEREFOR

(75) Inventors: Takahiro Koshihara, Tokyo (JP); Hiroharu Kato, Kobe (JP); Akio Nagamune, Chiba (JP)

(73) Assignee: JFE Steel Corporation (JP)

( * ) Notice: Subject to any disclaimer, the term of this patent is extended or adjusted under 35 U.S.C. 154(b) by 1010 days.

(21) Appl. No.: 12/935,307

(22) PCT Filed: Mar. 27, 2009

(86) PCT No.: PCT/JP2009/056914
§ 371 (c)(1),
(2), (4) Date: Nov. 3, 2010

(87) PCT Pub. No.: WO2009/123296
PCT Pub. Date: Oct. 8, 2009

(65) Prior Publication Data
US 2011/0040499 A1    Feb. 17, 2011

(30) Foreign Application Priority Data

Mar. 31, 2008  (JP) ................................ 2008-089364
Mar. 13, 2009  (JP) ................................ 2009-061501

(51) Int. Cl.
*G01N 21/00* (2006.01)
*G01N 21/892* (2006.01)
*G01N 27/83* (2006.01)
*G01N 21/89* (2006.01)

(52) U.S. Cl.
CPC .......... *G01N 21/892* (2013.01); *G01N 21/8922* (2013.01); *G01N 27/83* (2013.01); *G01N 2021/8918* (2013.01)

(58) Field of Classification Search
CPC . G01N 21/956; G01N 21/8922; G01N 27/82; G01N 2991/105; G01N 2991/106; G01N 2991/0234; G01N 2991/2632
USPC ........................................................... 702/35
See application file for complete search history.

(56) References Cited

U.S. PATENT DOCUMENTS 4,058,962 A * 11/1977 Spescha et al. ................. 57/265
4,463,425 A *  7/1984 Hirano et al. ................. 600/300
4,982,600 A *  1/1991 Kiso et al. ...................... 73/104

FOREIGN PATENT DOCUMENTS

JP          58-156842        9/1983
JP           6-324005       11/1994
(Continued)

*Primary Examiner* — Janet Suglo
*Assistant Examiner* — Michael Dalbo
(74) *Attorney, Agent, or Firm* — DLA Piper LLP (US)

(57) ABSTRACT

An apparatus for detecting periodic defects includes a sensor that obtains signals to evaluate properties of an area having a length longer than an expected defect period; a small area selector that separates small areas whose area length is shorter than that of the area so that all adjacent distance intervals are equal in a periodic defect arrangement direction, and selecting signals corresponding to the positions of the plurality of small areas from outputs from the sensor; an evaluation index calculator that calculates a similarity evaluation index between signal patterns among signals selected by the small area selector; a set value changer that changes the positions of the small areas and the distance interval, and repeating computational processings of the small area selector and the evaluation index calculator; and a period judgment device that judges the distance interval as a period when the evaluation index is higher than a value.

7 Claims, 16 Drawing Sheets

(56) References Cited

FOREIGN PATENT DOCUMENTS

| JP | 06324005 A | * | 11/1994 |
| JP | 7-198627 | | 8/1995 |
| JP | 8-160006 | | 6/1996 |
| JP | 08160006 A | * | 6/1996 |
| JP | 2006-105791 | | 4/2006 |
| JP | 2006-153614 | | 6/2006 |
| JP | 2006153614 A | * | 6/2006 |

* cited by examiner

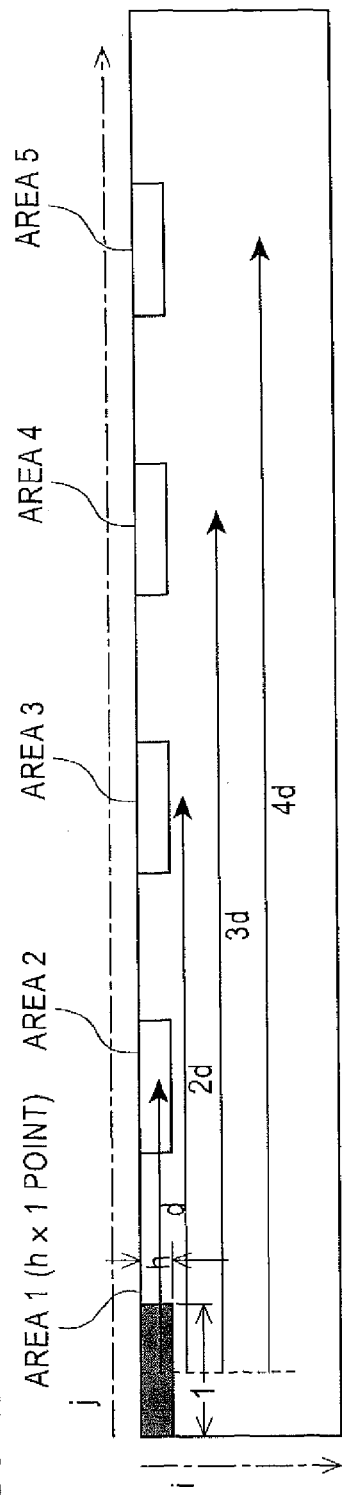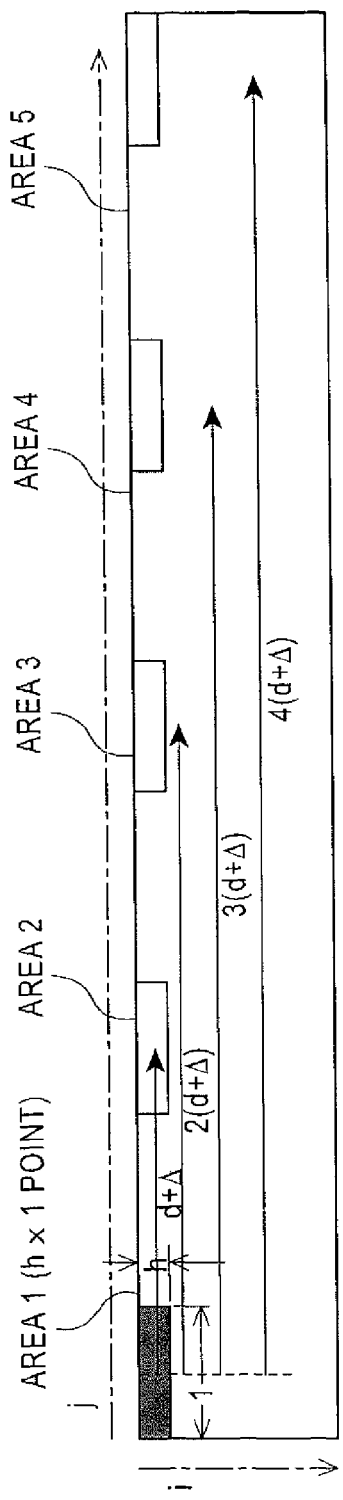

SINGLE PERIOD 50 mm x 8 mm AREA

PLURAL PERIODS 50 mm x 8 mm AREA

SINGLE PERIOD 100 mm x 8 mm AREA

PLURAL PERIODS 100 mm x 8 mm AREA

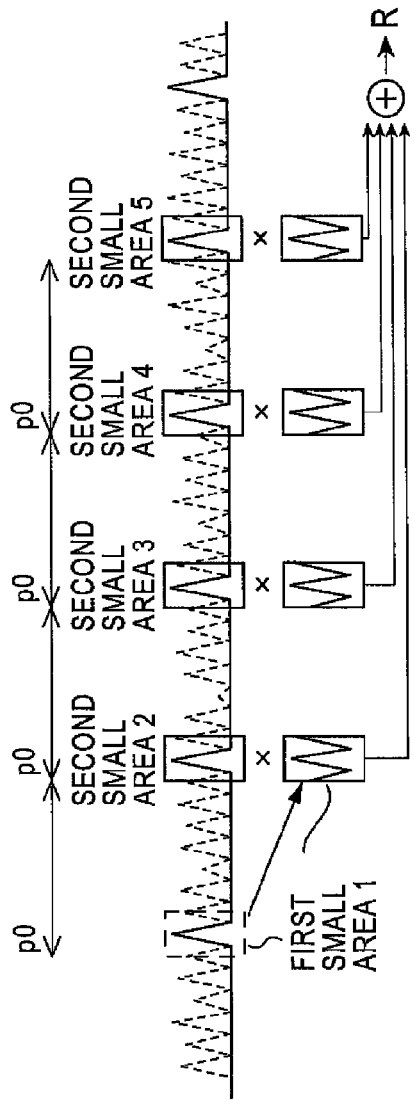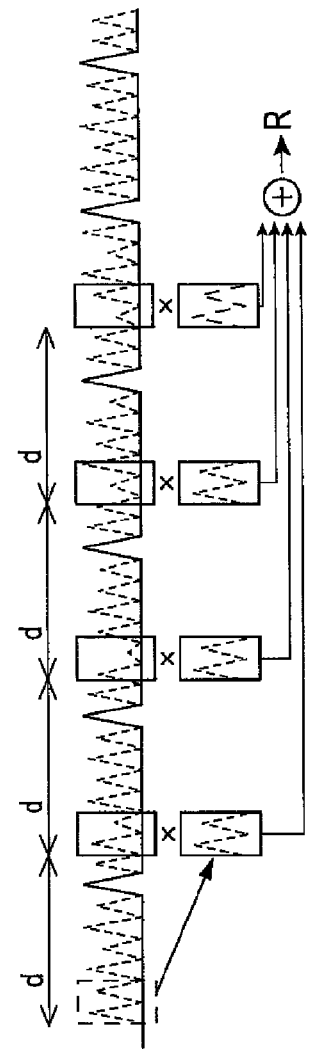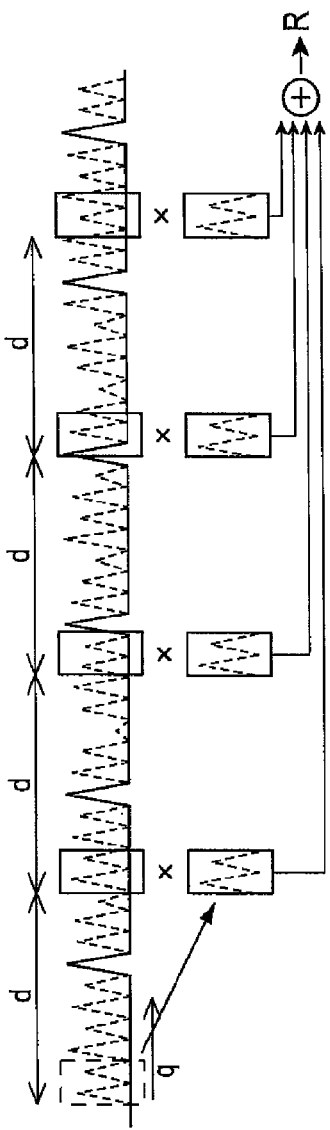

APPARATUS FOR DETECTING PERIODIC DEFECT AND METHOD THEREFOR

RELATED APPLICATIONS

This is a §371 of International Application No. PCT/JP2009/056914, with an international filing date of Mar. 27, 2009, which is based on Japanese Patent Application Nos. 2008-089364 filed Mar. 31, 2008 and 2009-061501 filed on Mar. 13, 2009, the subject matter of which is incorporated by reference.

TECHNICAL FIELD

This disclosure relates to a periodic defect detection apparatus that detects periodic defects periodically generating in belt-like bodies or columnar bodies formed of metal, plastics, or other materials and a method therefore.

BACKGROUND

In production lines of belt-like bodies or columnar bodies, a roll is sometimes used to convey products. When a certain trouble arises in a production process, defects originating from the roll are sometimes formed on a steel sheet. A method for detecting the defects will be described taking an example of a process for particularly producing a steel sheet.

In the production process of a steel sheet, periodic defects referred to as roll marks are sometimes formed. The roll marks are formed when foreign materials adhering to the roll provided in the production line or irregularities produced on the roll itself when the foreign materials bite into the roll are transferred to a steel sheet. The periodic defects are generated when the irregularities produced on the roll are transferred to a steel sheet. When generated once, the periodic defects are successively generated until the roll is exchanged or the process is improved. Therefore, it is extremely important also in terms of improvement in yield to discover the periodic defects at an early stage and to take a measure for dealing with the periodic defects.

Heretofore, many detection methods focusing on the periodicity of the periodic defects have been proposed as a method for detecting the periodic defects.

The technique disclosed in Japanese Unexamined Patent Application Publication No. 6-324005 is one of the methods utilizing the periodicity. According to that method, a target sample is measured by a defect detection sensor first, sensor output signals are subjected to synchronous addition at an expected period (length equivalent to one rotation of a final pressure roll in a steel line in JP 6-324005), and a defect signal having a period is emphasized from other noise components having no period. However, the method cannot be used for cases other than a case where the period is expected beforehand. For example, in the steel production line, the roll causing the defects is worn out, which changes the diameter of the roll in some cases. When the diameter varies, a defect development period naturally varies, and thus the above-described method is difficult to apply.

Heretofore, to deal with the problem such that the defect development period varies, some methods have been proposed.

Mentioned as a first method is a method including measuring a target sample by a defect detection sensor, subjecting sensor output signals to threshold treatment to extract a plurality of defect candidates, and comparing intervals between the plurality of defect candidates to judge that, when the intervals are in agreement with each other, the periodic defects are generated at the agreement interval as a period. However, when the method is actually applied, the following problems arise.

In an actual production line, a degree of contact between a roll and a steel sheet is not always constant. For example, the rolling reduction varies in a reduction roll. When the contact between the roll and the steel sheet is weak, a defect level is low. Therefore, a defect signal also becomes weak, and thus is not detected in some cases. Moreover, signals of slight unevenness, such as a sudden defect having no periodicity, surface roughness of a steel sheet that is originally harmless, or magnetic properties (in the case of a magnetic detection device), are detected, and they sometimes arise while being mixed with periodic defects. Therefore, the method for detecting periodicity simply by comparing the intervals between the defect candidates has problems in that the intervals between the defect candidates are not in agreement with each other due to non-defection of defect candidates or noises, such as sudden defects or over detection, and thus, periodic defects and the periodicity thereof cannot be accurately detected.

Known as a second method for dealing with the problem such that the defect development period varies is a detection method utilizing autocorrelation (e.g., Japanese Unexamined Patent Application Publication No. 58-156842).

The distance between peaks obtained based on computation results of autocorrelation represents a period of periodic signal components. Therefore, even when the period of the periodic signal components contained in a signal series to be processed is unknown, only the periodic signal components can be selectively extracted from the signal series buried in noise. However, the detection method utilizing autocorrelation also has a problem in that, when many noise components are contained in sensor output signals from a target sample, a periodicity judgment accuracy decreases. The detection method also has a problem in that, when a detection sensitivity is lowered so as to suppress the over detection, minor signals from minor defects cannot be detected.

Mentioned as a third method for dealing with the problem such that the defect development period varies is a detection method disclosed in Japanese Unexamined Patent Application Publication No. 2006-105791, for example.

The detection method includes successively picking up images of the surface of a moving belt-like body or the like, cutting out a template image T from the picked-up images, and comparing image similarity between the template image T and a target image G whose length in the longitudinal direction is longer than a target roll circumferential length to detect periodicity. According to the method, to accurately determine a defect period, correlations of not only defect parts but base-design parts of parts free from defects are calculated. Therefore, the image similarity is compared in the range equal to or more than one roll rotation. According to that method, in a stage of evaluating the image similarity between the template image and the target image, the similarity is evaluated by gradually shifting a relative position of the mutual images. Therefore, the method can be applied to the case where the diameter of the roll gradually varies due to abrasion. However, that method has problems in that the method cannot be applied to rolls other than a roll on which a base pattern is formed, i.e., a final reduction roll before inspection, because the base pattern of parts free from defects is utilized for obtaining period information.

In an actual production line of a steel sheet, it is necessary to detect not only defects originating from a roll generated in the final reduction roll before inspection but such defects that have been generated before. Specifically, in the case of cold rolling, it is necessary to detect defects in a reduction roll in one stage or two stages prior to the final reduction roll, defects in a roll in an annealing furnace prior to a final temper rolling roll in a CAL line, defects originating from the roll generated during cold rolling, etc. Therefore, it is necessary to detect defects generated in a plurality of rolls having different diameters. However, the detection method of JP 2006-105791 cannot be applied to the case.

It could therefore be helpful to provide a device for detecting periodic defects of a belt-like body or the like which can be used even when the defect development period varies and which can judge, with a high degree of accuracy, periodic defects generated not only in a reduction roll but in a plurality of rolls having different diameters, particularly even when the defects are minor, and a method therefor.

SUMMARY

We examined the problems of a former correlation operation. FIG. 18 schematically illustrates an example of a correlation operation to measurement signals of usual periodic defects. Utilizing the fact that a correlation coefficient value increases when signal wave forms of a reference signal and an input signal are completely in agreement with each other or have high similarity, the period of the periodic defects is determined from the interval between parts having a high correlation value. However, when applied to detection of periodic defects, a reference signal is cut out from an input signal (i.e., a sensor measurement signal in the case of defect detection) and created. Thus, as shown in FIG. 19, when the S/N of the input signal is low, the S/N of a correlation operation does not increase.

To avoid the above, we discovered for increasing the S/N focusing on a feature that, when a periodic defect is generated once, a plurality of defects are repeatedly generated (e.g., 5 times or more). The correlation operation has an advantage in that a period can be calculated based on data for one period, but is not computation utilizing data for a plurality of periods. In contrast, we found that improvement in S/N is achieved utilizing data for a plurality of periods.

We also found that a data area (number of data) in which a correlation operation is performed has a preferable range for further improvement in S/N. More specifically, it has been found to be preferable that the data area in which a correlation operation is performed contain data of defect signals in a higher proportion.

We thus provide:

An apparatus for detecting periodic defects comprises:

a sensor for obtaining signals for evaluating properties of an area having a length longer than an expected defect period on a target sample;

a small area selection means for separating a plurality of small areas whose area length is shorter than that of the area so that all distance intervals adjacent to one another are equal in a periodic defect arrangement direction to determine positions of the plurality of small areas, and selecting signals corresponding to the positions of the plurality of small areas from outputs from the sensor;

an evaluation index calculation means for calculating a similarity evaluation index between signal patterns among a plurality of signals selected by the small area selection means;

a set value changing means for changing the positions of the small areas and the distance interval, and repeating computational processings of the small area selection means and the evaluation index calculation means; and a period judgment means for judging the distance interval as a period when the evaluation index is higher than a value set beforehand.

In the apparatus for detecting periodic defects, the small area selection means is preferably as follows.

In the apparatus for detecting periodic defects, the small area selection means has:

a first small area selection means for determining one position of the small area whose length is shorter than the area to define the area as a first small area, and selecting a signal corresponding to the position of the first small area from the sensor output; and a second small area selection means for disposing a plurality of second small areas in a periodic defect arrangement direction on the basis of the position of the first small area while separating the second small areas so that all distance intervals are equal, and selecting signals corresponding to the positions of the plurality of second small areas from the sensor output, and the set point changing means changes the position of the first small area and the distance interval, and repeats computational processings of the small area selection means and the evaluation index calculation means.

In the apparatus for detecting periodic defects, the sensor is preferably a magnetic sensor that magnetizes a target sample formed of a magnetic metal component, and obtains a leakage flux signal.

In the apparatus for detecting periodic defects, it is preferable that the length of the small area be substantially the same as the length of an expected largest defect.

In the apparatus for detecting periodic defects, it is preferable for the evaluation index calculation means to calculate a value for evaluating similarity for each small area, and combine the values to determine the evaluation index.

In the apparatus for detecting periodic defects, it is preferable for the evaluation index calculation means to calculate a value for evaluating similarity for each small area, and add the values to obtain the evaluation index.

In the apparatus for detecting periodic defects, it is preferable that the value for evaluating similarity for each small area be a correlation value between the small areas.

An apparatus for detecting periodic defects comprises:

a sensor for obtaining signals for evaluating properties of a two-dimensional area whose length is longer than an expected defect period on a target sample;

a periodicity judgment means for obtaining a periodic defect candidate based on an output from the sensor; and a defect judgment means for judging at least the existence of a defect based on the defect candidate and the sensor output, in which the periodicity judgment means performs:

first computational processing for repeating a processing of selecting a first two-dimensional small area smaller than the two-dimensional area in the two-dimensional area, selecting a plurality of second two-dimensional small areas separated at a given distance in the periodic defect arrangement direction from the first two-dimensional small area in such a manner as to have the same size as the first two-dimensional small area, calculating a similarity evaluation index between signal patterns of the sensor outputs corresponding to the two-dimensional small areas, respectively, to evaluate similarity, and judging that, when the similarity is evaluated to be high, a defect candidate exists in each two-dimensional small area at the distance as a period, while changing the distance, and second computational processing for repeating the first computational processing until the first two-dimensional small area covers a given range in the original two-dimensional area while changing the position of the first two-dimensional small area in the original two-dimensional area when the first computational processing is repeated until the distance covers the range of a period where the periodic defect may be generated.

A method for detecting periodic defects comprises:

(a) a signal inputting step of obtaining sensor outputs for evaluating properties of an area whose length is longer than that of an expected defect period on a target sample, (b) a small area selecting step of separating a plurality of small areas whose area length is shorter than that of the area so that all distance intervals adjacent to one another are equal in a periodic defect arrangement direction to determine positions of the plurality of small areas, and selecting signals corresponding to the positions of the plurality of small areas from the sensor outputs;

(c) an evaluation index calculation step of calculating a similarity evaluation index between signal patterns among a plurality of signals selected in the small area selecting step;

(d) a set value changing step of changing the positions of the small areas and the distance interval, and repeating (b) and (c) above; and (e) a period judging step of judging the distance interval to be a period when the evaluation index determined in (c) above is higher than a value set beforehand.

In the periodic defect detection method, the small area selecting step is preferably as follows.

In the method for detecting periodic defects, the small area selecting step determines one position of the small area whose length is shorter than the area to define the area as a first small area, disposes a plurality of second small areas in a periodic defect arrangement direction on the basis of the position of the first small area while separating the second small areas so that all distance intervals are equal, and selects signals corresponding to the position of the first small area and the positions of the plurality of second small areas from the sensor outputs, and the set point changing step repeats (b) and (c) above while changing the position of the first small area and the distance interval.

The method for detecting periodic defects includes:

a first step of obtaining sensor outputs for evaluating properties of a two-dimensional area whose length is longer than an expected defect period on a target sample;

a second step of repeating a processing of selecting a first two-dimensional small area smaller than the two-dimensional area in the two-dimensional area, selecting a plurality of second two-dimensional small areas separated at a given distance in the periodic defect arrangement direction from the first two-dimensional small area in such a manner as to have the same size as the first two-dimensional small area, calculating a similarity evaluation index between signal patterns of the sensor outputs corresponding to the two-dimensional small areas, respectively, to evaluate similarity, and judging that, when the similarity is evaluated to be high, a defect candidate exists in each two-dimensional small area at the distance as a period, while changing the distance;

a third step of repeating the second step until the first two-dimensional small area covers a given range in the original two-dimensional area while changing the position of the first two-dimensional small area in the original two-dimensional area when the first computational processing is repeated until the distance covers the range of a period where the periodic defect may be generated; and a fourth step of judging at least the existence of a defect based on the defect candidate and the sensor output.

The apparatus has a sensor for obtaining signals for evaluating properties of an area having a length longer than an expected defect period on a target sample; a small area selection means for separating a plurality of small areas whose area length is shorter than that of the area so that all distance intervals adjacent to one another are equal in a periodic defect arrangement direction to determine positions of the plurality of small areas, and selecting signals corresponding to the positions of the plurality of small areas from outputs from the sensor; an evaluation index calculation means for calculating a similarity evaluation index between signal patterns among a plurality of signals selected by the small area selection means; a set value changing means for changing the positions of the small areas and the distance interval, and repeating computational processings of the small area selection means and the evaluation index calculation means; and a period judgment means for judging the distance interval as a period when the evaluation index is higher than a value set beforehand. Therefore, even when the defect development period fluctuates, the defects can be easily detected and minor signals from minor periodic defects generating in rolls having various diameters can be detected with high accuracy.

The method has (a) a signal inputting step of obtaining sensor outputs for evaluating properties of an area whose length is longer than that of an expected defect period on a target sample, (b) a small area selecting step of separating a plurality of small areas whose area length is shorter than that of the area so that all distance intervals adjacent to one another are equal in a periodic defect arrangement direction to determine positions of the plurality of small areas, and selecting signals corresponding to the positions of the plurality of small areas from the sensor outputs; (c) an evaluation index calculation step of calculating a similarity evaluation index between signal patterns among a plurality of signals selected in the small area selecting process; (d) a set value changing step of changing the positions of the small areas and the distance interval, and repeating (b) and (c) above; and (e) a period judging step of judging the distance interval to be a period when the evaluation index determined in (c) above is higher than a value set beforehand. Therefore, even when the defect development period fluctuates, the defects can be easily detected and minor signals from minor periodic defects generating in rolls having various diameters can be detected with high accuracy.

BRIEF DESCRIPTION OF THE DRAWINGS

FIGS. 4A and 4B are explanatory views of a computational processing by the periodicity judging device.

FIGS. 20A to 20C are explanatory views illustrating the principle of the periodic defect detection method.

Figure 1:
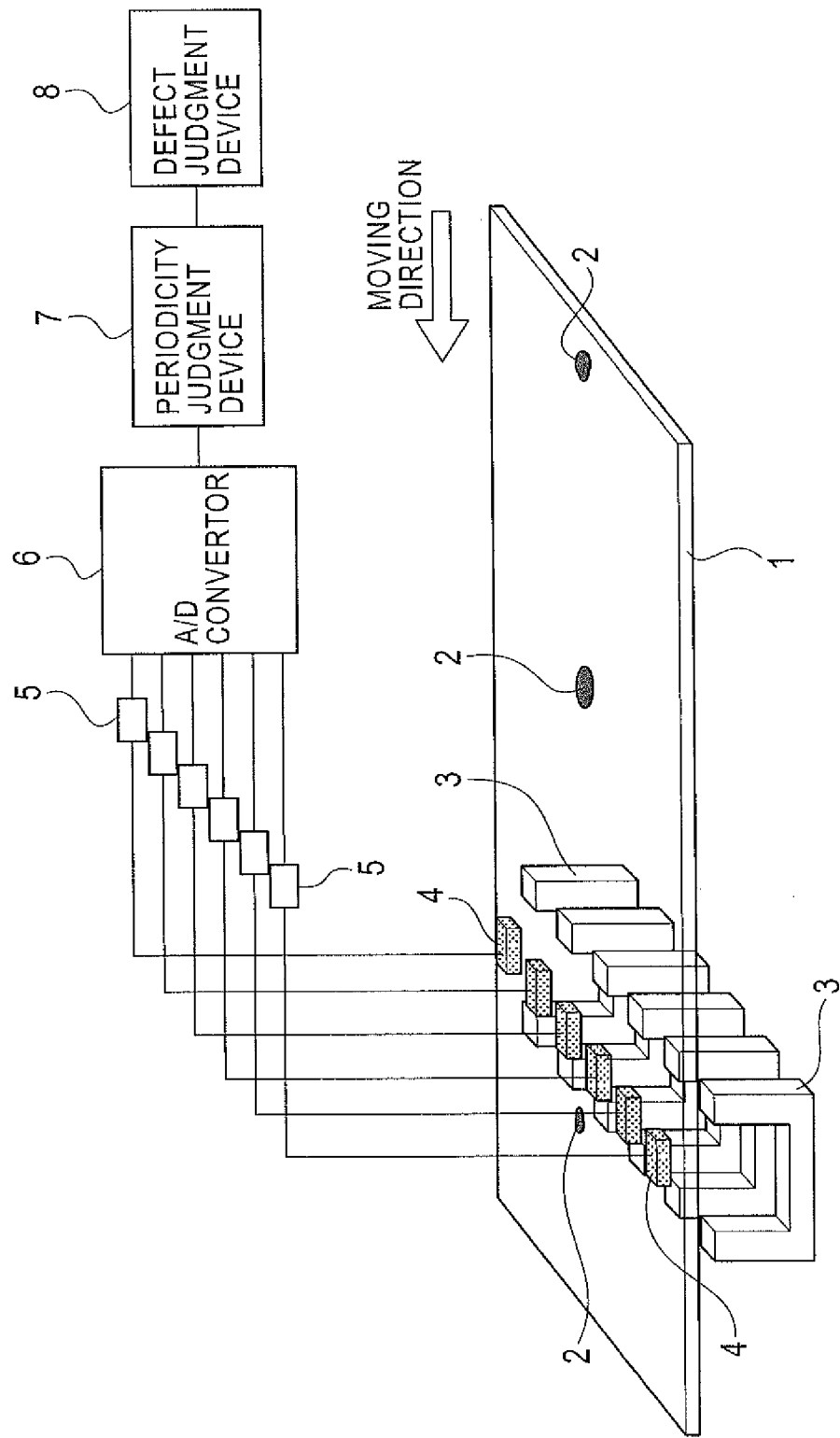
FIG. 1 is a block diagram of a periodic defect detection device according to a first example.

| Reference Numerals | | |
|---|---|---|
| 1 steel sheet, | 2 defect, | 3 magnetizer |
| 4 magnetic sensor, | | 5 signal preprocessing device |
| 6 A/D converter, | | 7 periodicity judging device |
| 8 defect judging device, | | 71 data storage area |
| 72 first small area selection unit | | |
| 73 first small area data setting unit | | |
| 74 second small area selection unit | | |
| 75 second small area data setting unit | | |
| 76 similarity evaluation index computation unit | | |
| 77 period judgment unit, | | |
| 78 judgment result storing unit | | |

DETAILED DESCRIPTION

The detection principle of a periodic defect will be described with reference to FIGS. 20A to 20C.

For ease of understanding, FIGS. 20A to 20C illustrate using a one-dimensional data row, but can be applied to the case of a two-dimensional data row as mentioned later. First, as shown in FIG. 20A, the case where a first small area 1 containing a defect is taken, and second small areas 2, 3, 4, and 5 (here, four areas are taken, but the number of the second small areas is not limited) having the same size as the first small area are taken on the data row at the same interval as a defect period $P_0$ (referring to a distance interval obtained by adding the size of the small area and a distance interval between separated small areas adjacent to one another) is taken as an example. When a product-sum operation of the first small area 1 and each of the second small area 2, 3, 4 and 5 is performed, each of the obtained four correlation values is large. Furthermore, a value obtained by adding these four correlation values is calculated as a similarity evaluation index R.

Thus, as shown in FIG. 20A, when a defect position is contained in the first small area and a distance interval d is exactly in agreement with the defect period $P_0$, all the correlation values become large. Thus, the similarity evaluation index R relating thereto surely becomes a large value. In contrast, when a defect is not contained in the first small area or the distance interval d is not in agreement with the defect period $P_0$, all the values do not become large even when any of the correlation values happens to be large. Thus, the similarity performance index R does not become large. For example, as shown in FIG. 20C, the similarity evaluation index R for each set distance interval d is determined while gradually changing the distance interval d as represented by d' (=d+Δd). When the distance interval d covers a given range (e.g., to the maximum length of an expected defect period), the calculation of the similarity evaluation index R is repeated while changing the position q of the first small area in the same manner as above. Then, the periodic defect period is determined from the distance interval d in the case where the similarity evaluation index R becomes larger than a value set beforehand or becomes the maximum value.

The principle is describe as above, and will be described in detail with reference to the following examples.

EXAMPLE 1

FIG. 1 is a schematic view of a periodic defect detection device according to a first example. FIG. 1 includes a steel sheet 1 (which is shown in a perspective view so that devices disposed under the steel sheet are easily recognized), a periodic defect 2, a magnetizer 3, a magnetic sensor 4, a signal preprocessing device 5 containing an amplifier and a filter circuit, an A/D converter 6, a periodic defect detector 7, and a defect judging device 8.

It is supposed that, in this example, a plurality of roll-causing surface defects originating from a reduction roll exists as the periodic defect 2 in the rolling direction (moving direction in FIG. 1) in the steel sheet 1. More than one pair of the magnetizer 3 and the magnetic sensor 4 are disposed facing with each other across the steel sheet 1 along the width direction (direction orthogonal to the periodic defect arrangement direction) of the steel sheet 1. The magnetizer 3 is magnetized by a direct current applied thereto from a magnetization power source (not shown). The magnetic flux generated by the magnetizer 3 between both the magnetic poles passes through the steel sheet 1. The magnetizer 3 is disposed so that the magnetic flux flows in the width direction of the steel sheet 1. A pair of the magnetizer and the magnetic sensor is disposed facing with each other across the steel sheet 1, but may be provided on the same side. When the periodic defects 2 exist in the steel sheet 1, the magnetic flux is hindered by the periodic defect 2. The change in the magnetic flux can be detected by the magnetic sensor 4.

In the example of FIG. 1, the moving direction shown in FIG. 1 corresponds to the periodic defect arrangement direction. Thus, the periodic defect 2 reaches the position of the magnetic sensor 4 in accordance with the movement of the steel sheet 1 conveyed by a rolling line or the like. Then, signals change each time. Therefore, when measurement signals of the magnetic sensor 4 are collected as a serial data according to the movement amount (i.e., position of the steel sheet 1) in the moving direction of the steel sheet, measurement data (signals for evaluating properties) in the arrangement direction of the periodic defects 2 can be obtained.

It is necessary to obtain measurement data for a distance (moving distance of the steel sheet) longer than that of the maximum value (based on the maximum roll circumferential length when a plurality of reduction rolls are provided) of an expected defect period of the periodic defects 2. Thus, it may be structured so that measurement data for a plurality of periods, e.g., about 3 to 5 periods, is obtained. However, the structure is not limited thereto. As described later, the S/N is improved by performing computation while increasing the number of the periods, and then collecting data. Thus, the upper limit may be suitably determined in accordance with a degree of a signal S/N of a measurement target.

In the case of a sensor capable of measuring the steel sheet 1 over the entire width direction at one time, the measurement can be performed throughout the entire length in the longitudinal direction of the steel sheet 1. Thus, in such a case, a plurality of periods are measured, causing no problems. In general, in the case of periodic defect inspection, a sensor of measuring only a part of the steel sheet 1 in the width direction is employed, and the measurement is performed by traversing the sensor from the viewpoint of cost in some cases. In such a case, the measurement is performed for the periods set above at the same width position (length equal to or longer than a plurality of lengths of the maximum period, e.g., about 3 to 5 periods), and then the width position may be moved.

The output signals thus obtained of the magnetic sensor 4 are amplified by the amplifier built into the signal preprocessing device 5, noise is removed in a filter circuit built into the signal preprocessing device 5, and then the signals are sent to the A/D converter 6.

Figure 2:
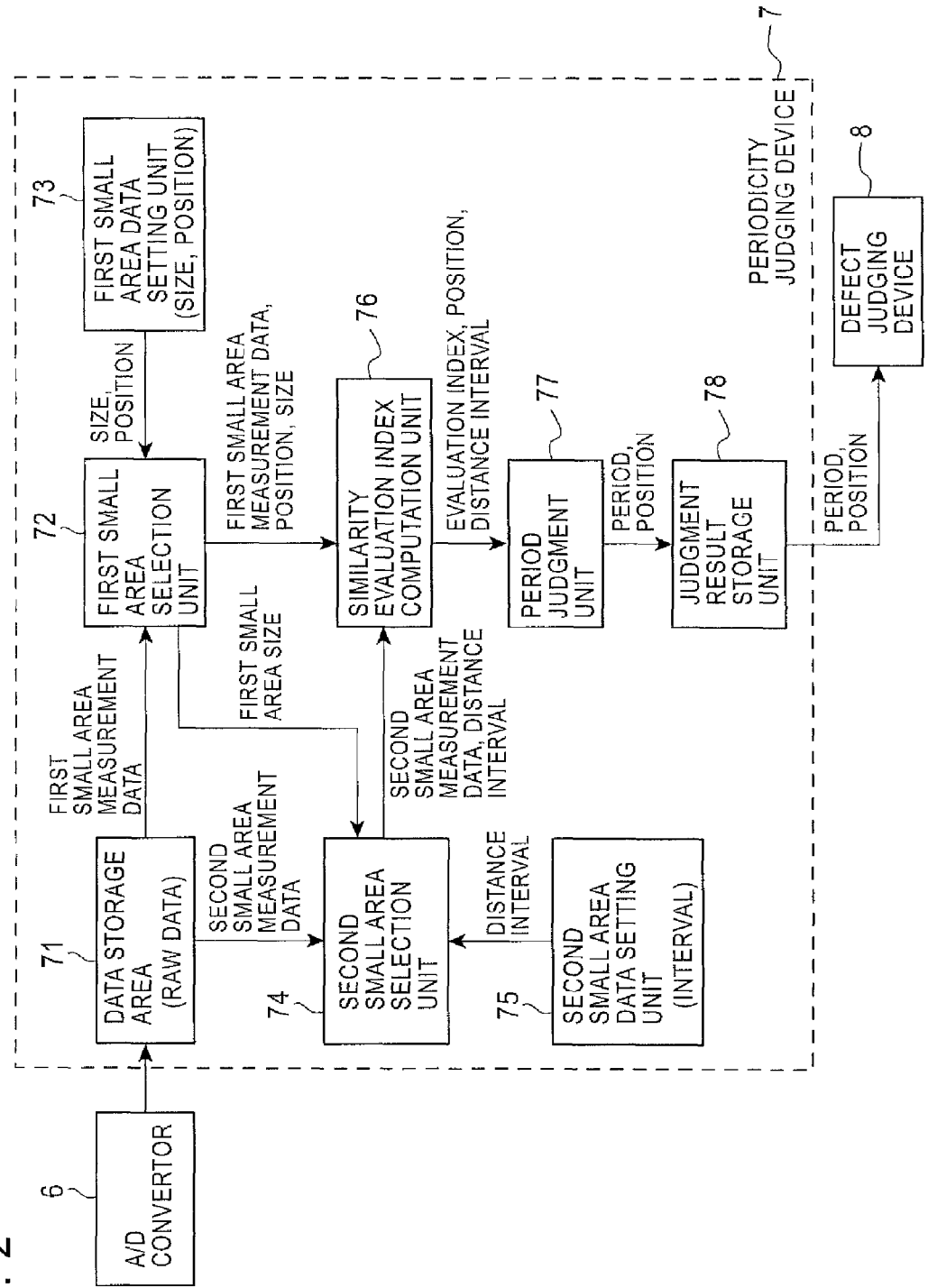
FIG. 2 is a view of an example of a functional block of a periodicity judging device of the first example.

In the A/D converter 6, the analog signal is sampled and digitized so that the pitches are equal to each other on the steel sheet 1. For example, a sampling pulse can be obtained by, for example, bringing a rotary encoder into contact with the steel sheet 1. The data digitized by the A/D converter 6 are sent to the periodicity judging device 7. Periodicity judgment shown in FIG. 2 is performed. A sampling pitch as used herein refers to a spatial resolution when a signal of the magnetic sensor 4 is converted to digital data, and stored in a data memory, and may be set to a value (e.g., ½ of the smallest length or lower) allowing detection of the smallest length of a defect as a detection target.

FIG. 2 is an explanatory view of an example of a functional block view of the periodicity judging device 7.

The periodicity judging device 7 has a data storage area 71 for memorizing raw data of the A/D-converted measurement data as they are (here, a two-dimensional data row because a plurality of magnetic sensors 4 are disposed in the width direction), a first small area selection unit 72 for selecting data of the first small area, a first small area data setting unit 73 for setting the size and position of the small area at the time of selecting the data of the first small area, a second small area selection unit 74 for selecting data of a second small area, a second small area data setting unit 75 for setting the size and distance interval of the second small area at the time of selecting the data of the second small area, a similarity evaluation index computation unit 76 for calculating a similarity evaluation index by inputting the data selected from the first small area selection unit and the second small area selection unit, a periodicity judgment unit 77 for judging the existence of periodicity from the similarity evaluation index, and a judgment result storage unit 78 for storing the judgment results, and outputting the results to a defect judgment unit.

In the first small region data storage unit 73, the position of the first small region is successively changed, and set in the first small region selection unit. In the second small region data storage unit 75, the distance interval of the second small region is successively changed, and the position of the second small region is set in the second small region selection unit 74.

Then, computation of the similarity performance index is repeatedly performed. The size of the small area is fixed while repeatedly performing the computation. A value of the size of the small area set in by the first small area data selection unit 73 is output to the second small area selection unit 74, and is set to the same value. When the calculated evaluation index is evaluated to be a high similarity value, the periodic judgment unit 77 determines periodicity from the distance interval at that time and the area where a periodic defect candidate exists from the position at that time.

Figure 3:
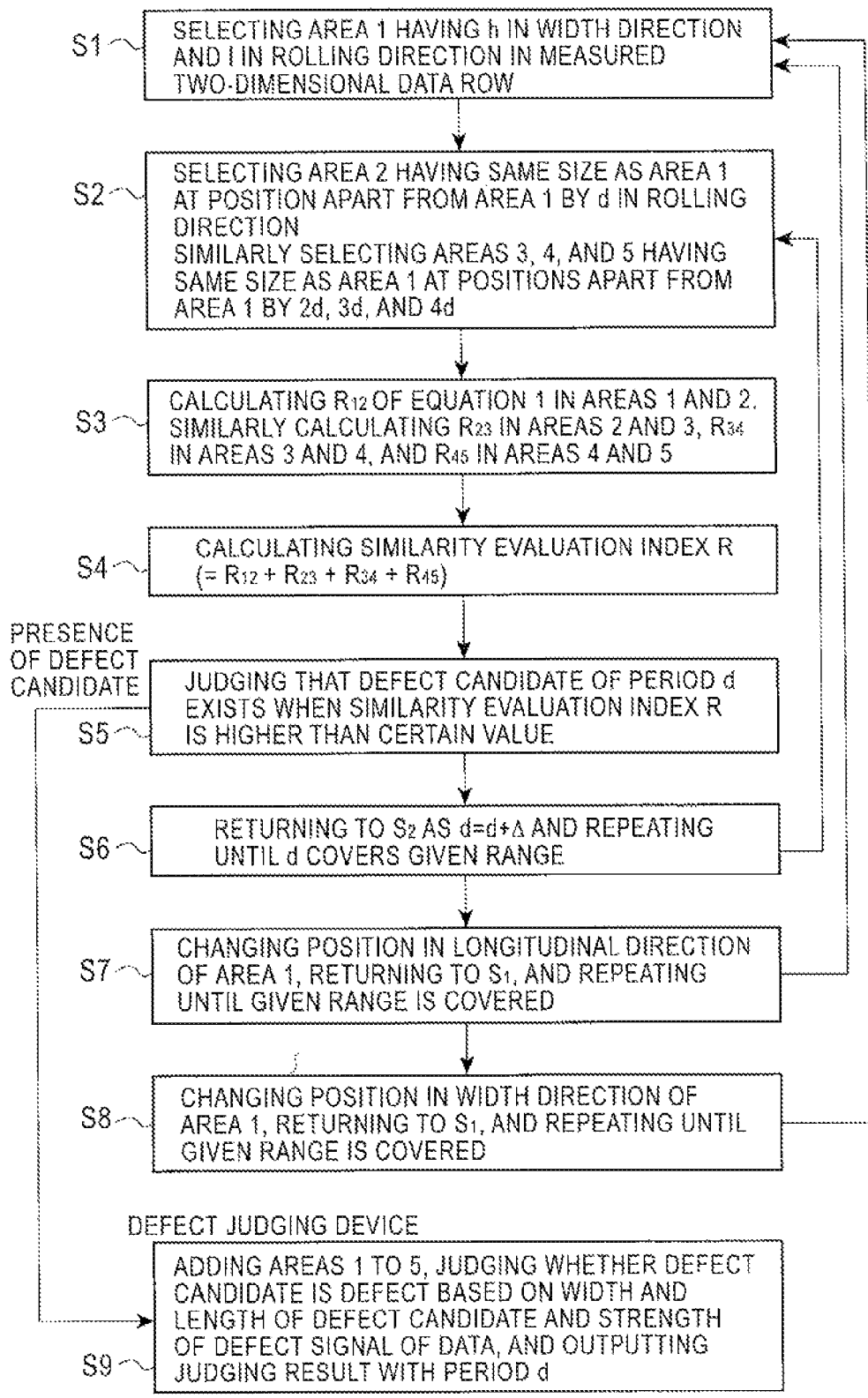
FIG. 3 is a flowchart of a process of the periodicity judging device and the defect judging device of the first example.

FIG. 3 is a flowchart of a process of the periodicity judging device 7 and the defect judging device 8. FIGS. 4A and 4B are explanatory views of computational processings thereof.

(S1) As shown in FIG. 4A, the first small area selection unit 72 selects h in the width direction and an area 1 (reference region) having a size of 1 in the rolling direction in the measured range. The initial value of d used in Step S2 and the following steps described later may be set to a value of the smallest roll circumferential length (minimum value of a periodic defect).

(S2) As shown in FIG. 4A, the second small area selection unit 74 selects an area 2 having the same size as the area 1 at the same position as the area 1 in the width direction and at a position apart from the area 1 by the distance d in the rolling direction as viewed from the area 1. Similarly, an area 3 is selected at a position apart from the area 1 by a distance 2d, an area 4 is selected at a position apart from the area 1 by a distance 3d, and an area 5 is selected at a position apart from the area 1 by a distance 4d.

The area 1 corresponds to the first small area and the areas 2 to 5 corresponds to the second small area.

(S3) The similarity evaluation index computation unit 76 calculates Equation 1 at a position where the areas 1 and 2 are corresponding to each other to calculate a correlation value $R_{12}$ of the areas 1 and 2. In Equation 1, x (i, j) is a value at the i-th position in the width direction and the j-th position in the rolling direction in the total range where the digitized sensor outputs are measured.

$$R_{12} = \sum_i \sum_j x(i, j) * x(i, j+d) \qquad \text{(Equation 1)}$$

Similarly, Equation 2 is calculated, and correlation values R23, R34, and R45 are obtained at corresponding parts of the areas 2 and 3, the areas 3 and 4, and the areas 4 and 5.

$$\left. \begin{array}{l} R_{23} = \sum_i \sum_j x(i, j+d) * x(i, j+2d) \\ R_{34} = \sum_i \sum_j x(i, j+2d) * x(i, j+3d) \\ R_{45} = \sum_i \sum_j x(i, j+4d) * x(i, j+5d) \end{array} \right\} \qquad \text{(Equation 2)}$$

(S4) The similarity evaluation index computation unit 76 calculates Equation 3), and adds the correlation values R12, R23, R34, and R45, thereby determining the similarity evaluation index R. Here, the processing aims at eliminating influences of variation or deviation for each area of a plurality of areas whose correlation values are added, and is a specific processing of detecting a periodic defect.

$$R = R_{12} + R_{23} + R_{34} + R_{45} \qquad \text{(Equation 3)}$$

(S5) The periodicity judgment unit 77 judges that there is a periodic defect candidate when the similarity evaluation index R is equal to or higher than the threshold set beforehand.

(S6) Next, as shown in FIG. 4B, the distance d as a basis between the areas whose correlation values are calculated is changed to d+Δ(d+Δ=d). Then, Steps S2 to S5 are repeated. Here, A is a fixed number smaller than the size 1 in the rolling direction of a given area. In order to evaluate without omission, Δ<1<2 is preferable. The changing range of d is adjusted to the range where periodic defects may be generated (given range of S6 of FIG. 3). In a line of the steel sheet 1, it is preferable that the range cover the circumferential direction of a roll provided in the line where a roll mark may be generated. The d may be changed in the range around an expected circumferential length of each roll (e.g., range of about several 10 mm). Therefore, when the circumferential direction of each roll in the line is remarkably different from each other, and there is a range where periodic defects are not generated, it is not necessary to set the value of d in the range.

(S7) The position q of the area 1 as the basis of similarity evaluation is shifted by Δq in the rolling direction, and S1 to S6 above are repeated. One shift amount Δq at this time is preferably smaller than ½ of the size 1 in the rolling direction of the area for evaluation without omission. The lower limit of the shift amount Δq is a sampling period in the rolling direction where the digitized sensor outputs are measured, but may be suitably determined because it takes time to perform the computation. Then, by repeating S1 to S6 above until the position q of the area 1 becomes the maximum defect period value (maximum roll circumferential length) (until a given range of S7 of FIG. 3 is covered), the evaluation can be performed without omission. The initial value of d is set to the smallest roll circumferential length in Step S1 above. However, when the value of q becomes larger than the smallest roll circumferential length, the initial value of d in S1 may be set to the value of q. More specifically, when the computation is always performed until the value of the position q reaches the maximum defect period value (value of the maximum roll circumferential length) from 0, the calculation is overlapped in the range where the q exceeds the d. Thus, when the calculation is not performed in the case where the q exceeds the d, efficient calculation can be performed. Thus, such calculation is preferable.

(S8) S1 to S7 above are repeated while shifting the position of the area 1 serving as the basis of the similarity evaluation in the width direction. The shift amount at this time is preferably smaller than ½ of the size h in the width direction of the area for evaluation without omission.

(S9) When it is judged that there is a periodic defect candidate in the judgment of S5 as a result of performing the above periodicity evaluation, signal data of the positions in the rolling direction and the width direction, the length of a period, and the area of the periphery of the defect candidate are stored in the judgment result storage unit 78 and are transmitted to the defect judging device 8. The positions in the rolling direction and the width direction of the defect candidate are determined from the position of the area 1 (or the area 2, 3, 4, or 5).

The defect judging device 8 judges whether the defect candidate is a defect from numerical values of the signal strength, length in the width direction, length in the rolling direction, and defect shape of the defect candidate, and outputs the result with the period d obtained by the periodicity judging device 7 when the defect candidate is judged to be a defect. In the defect judging device 8, the judgment may be performed after the S/N is improved by subjecting signals of a defect part to synchronous addition based on the period obtained by the periodicity judging device 7. Then, S9 is completed, the process returns to Step S6.

The flowchart is an example of the procedure and the procedure may be suitably changed. For example, the interval d is repeatedly changed in the process of repeatedly changing the position of the area 1, and may be vice versa. It has been described that the evaluation of the similarity evaluation index R of S5 is performed whenever the similarity performance index R is calculated. However, the evaluation of the similarity performance index R may be performed after all the repetitions are completed. When the one-dimensional data are targeted, it is not necessary to change the position in the width direction of the data area 1 of S8.

When the signals of the defect part are subjected to synchronous addition by the defect judging device 8, the synchronous addition may be performed in the range having the same size (or substantially the same) as the area 1. This is because the position and the period of the defect candidate are clarified in the prior step. Most briefly, it can be realized by adding signals of the areas 1, 2, 3, 4, and 5 at the time when it is judged that the defect candidate is contained. Equation 4 represents an equation for calculating a synchronous addition value $y(i,j)$. When a value of $y(i,j)$ exceeds a specified value, the candidate is judged to be a defect. The calculation can be simplified by performing thus. In particular, since addition between narrow areas is simply performed, the calculation amount can be remarkably saved. Moreover, based on the data that are judged to have no periodic defects in S5, a noise level N is determined on-line. When $y(i,j)$ exceeds 3N, for example, the candidate may be judged to be a defect (i.e., judged to be a defect in the case of S/N>3). The N may be determined based on the maximum value or average square error of a given area.

$$y(i,j)=x(i,j)+x(i,j+d)+x(i,j+2d)+x(i,j+3d)+x(i,j+4d) \quad \text{(Equation 4)}$$

When the defect ha a spread in the width direction, the S/N is improved by performing integration in the width direction for the same position in the rolling direction. Thus, such a case is preferable.

As described above, in the first example, by performing the above-described processing, defects can be easily detected even when the defect development period fluctuates and minor signals from minor periodic defects generated in rolls having various diameters can be detected with high accuracy.

EXAMPLE 2

To increase accuracy for discriminating a harmless part of a defect, the resolution of the defect signal is generally increased. In our apparatus and methods, as described in the first example, the judgment processing (i.e., detection of a periodic defect candidate) of judging whether a periodic component is contained in the measurement signal is performed as a first stage. Then, when the periodic component is contained (when the periodic defect candidate is detected), the defect signal judging the degree of harmfulness of the defect utilizing the information of the period or generation position of the defect is emphasized, and the type, degree, and the like of the defect are judged as a second stage.

First stage: Detection of periodic defect candidate (Judgment of existence of periodic component)

Detection of defect candidate (Step S5) by periodicity evaluation (Repetition of similarity evaluation by a correlation operation: Steps S1 to S8 above)

Second stage: Judgment of degree of harmfulness of defect

It is judged whether the defect candidate is a defect or harmless by performing defect judgment (Step S9).

Thus, the processing is performed in two stages, and a final defect judgment is performed in the second stage. Accordingly, the evaluation may be roughly performed (over detection may be frequently performed) while lowering the resolution on the computation in the periodicity evaluation in the first stage. More specifically, the load of the computational processing is reduced by performing thus, and the processing rate can be increased.

The processing method will be described below. The procedure of the second example is the same as that of FIG. 3 described in the first example and is performed in a stage prior to S1. Thus, the same description as the first example is omitted.

Figure 5:
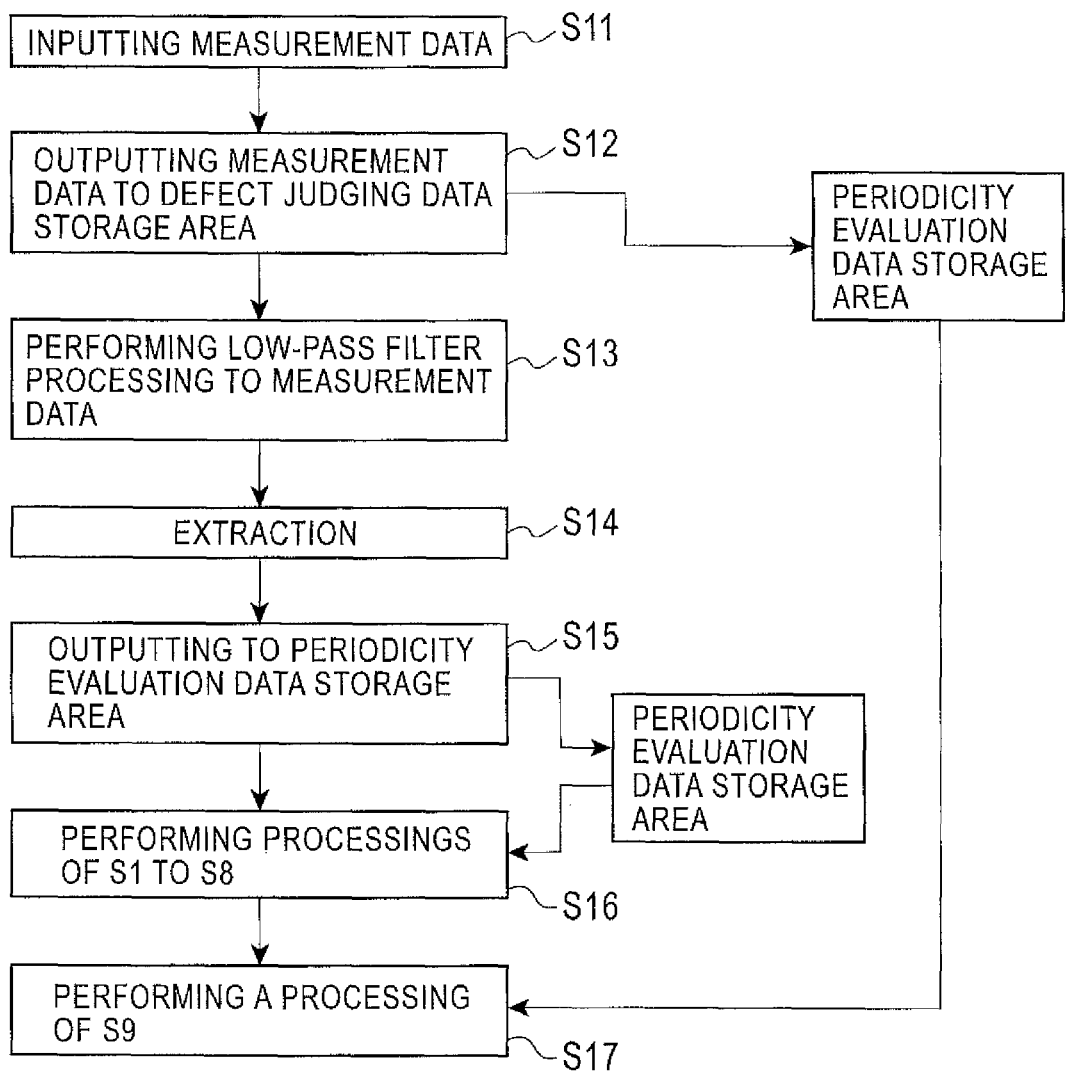
FIG. 5 is a flowchart of a process of a periodicity judging device and a defect judging device of a second example.

FIG. 5 is a flowchart illustrating the process of the periodic judging device 7 and the defect judging device 8 according to the second example.

(S11) A sampling pitch is measured as a value capable of detecting the smallest length of a detection target defect, and the measurement data are input.

(S12) The measurement data are stored as they are in the data storage area 71 of FIG. 2 and are stored once as they are in a storage area for storing data for judging the degree of harmfulness of a defect (data memory or the like) (not shown) which is prepared for judging the degree of harmfulness of a defect.

(S13) An LPF (Low Pass Filter; moving average may be acceptable) is used in the rolling direction of the input data (measured signal). This is performed to enable defect detection even when the defect position and the sampling position are shifted because the data are extracted at the time of performing periodicity computation in the following step. More specifically, this is performed to leave the defect signal information in the data left behind after the data extraction, considering a possibility that the defect signal does not remain when the data extraction is performed while the measurement data remaining as they are.

(S14) Periodicity evaluation data is created in which the signals are extracted at a rate of 1 in several sampling pitches (e.g., at a rate of 1 in 4 times or 1 in 2 to 8 times) at which the data created in S13 are measured.

(S15) The periodicity evaluation data created in S14 are stored in the data storage area 71 of FIG. 2.

(S16) Thereafter, Steps S1 to S8 are performed in the same manner as the first example. In (S15), when the periodicity evaluation data storage area for storing the periodicity evaluation data is provided other than the data storage area 71 and the periodicity evaluation data are stored therein, the computation is performed using the data stored in the periodicity evaluation data storage area in place of the data of the data area 71.

(S17) When it is judged that there is periodicity, the defect judgment is performed by performing the processing of S9 described in the first example using the data of the storage area for the data judging the degree of harmfulness of the defect.

Figure 6A:
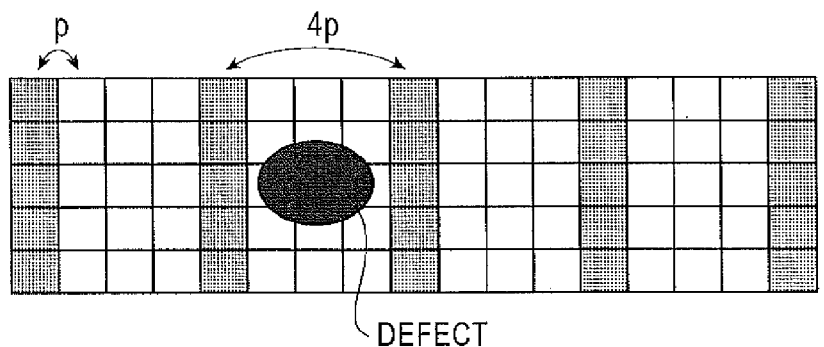
FIGS. 6A to 6C are explanatory views of the relationship between a data sampling pitch and defect detection.

In the case of two-dimensional data, when successively extracted in the width direction at the same position in the rolling direction (data are used in a striped pattern in the width direction), the defect is easily omitted depending on the timing as shown in FIG. 6A. To avoid such a condition, the smallest defect width of a detection target defect is defined as w and the spatial resolution in the width direction of the measurement signal is defined as w/2, for example, defect signals are obtained at least two data positions in the width direction. When defined as w/4, defect signals are obtained at four data positions in the width direction.

Figure 6B:
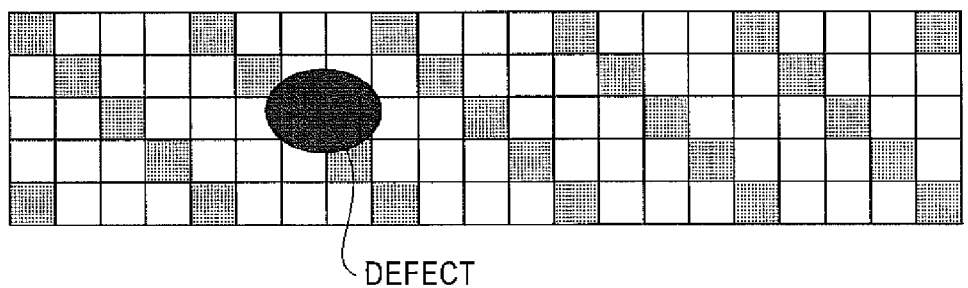

Thus, it is structured that the defect signals are obtained from a plurality of data positions in the width direction, and then are extracted while shifting the position in the rolling direction in the width direction as shown in FIG. 6B, for example, whereby the omission of the defect is suppressed.

Figure 6C:
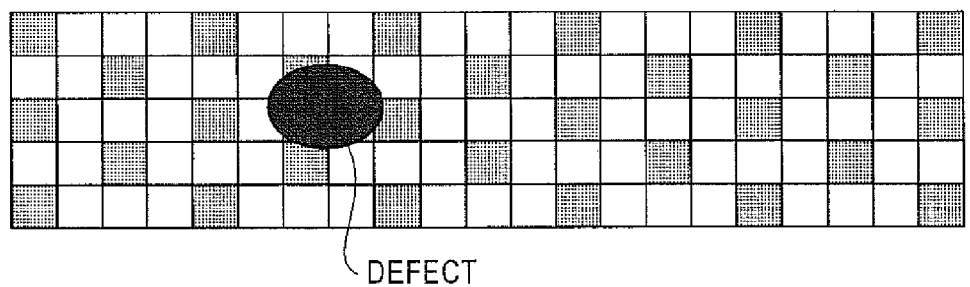

The shift amount may not be necessarily equivalent to one data position as shown in FIG. 6C.

EXAMPLE 3

Figure 7:
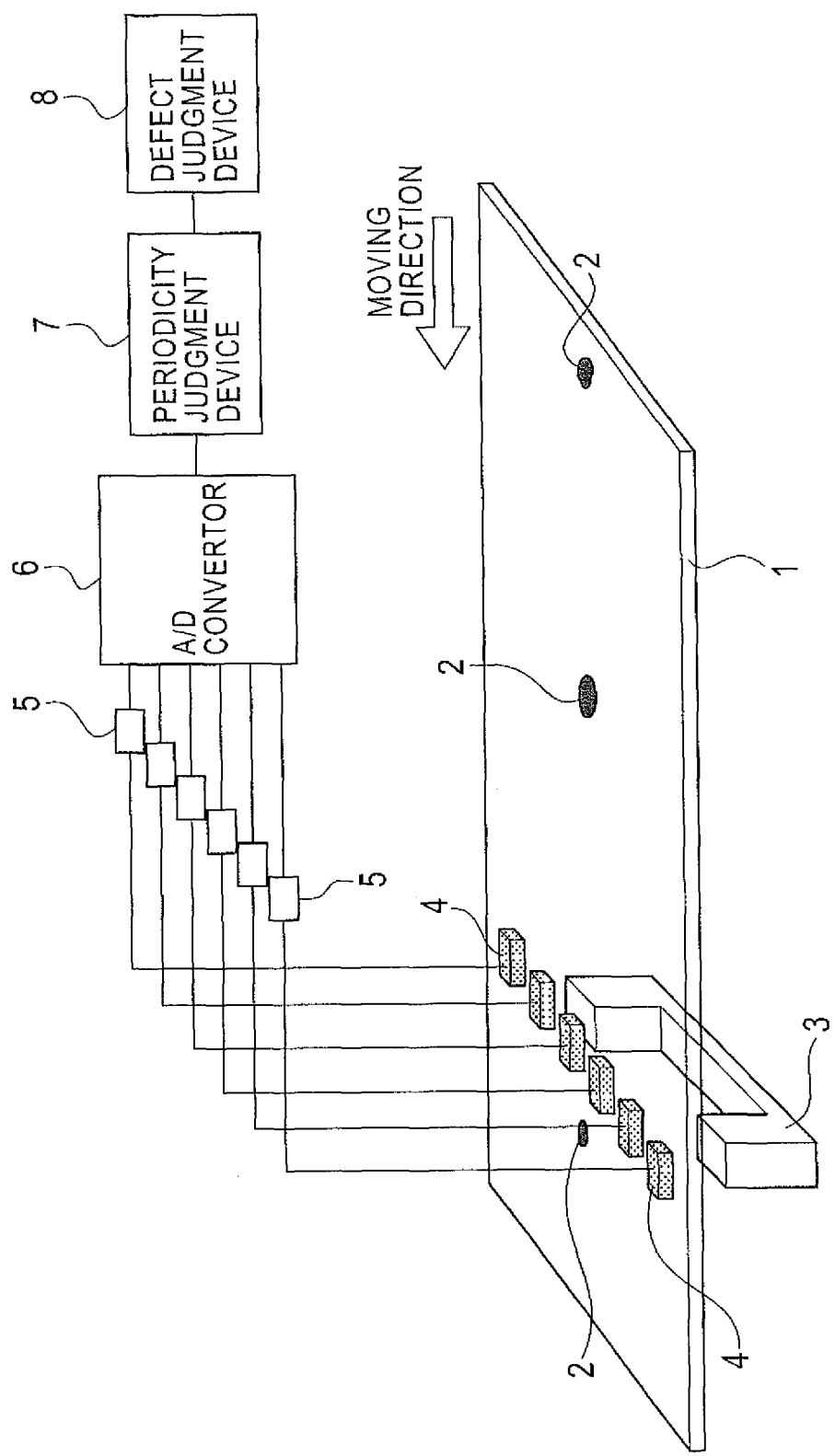
FIG. 7 is a block diagram of a periodic defect detection device according to a third example.
Figure 8:
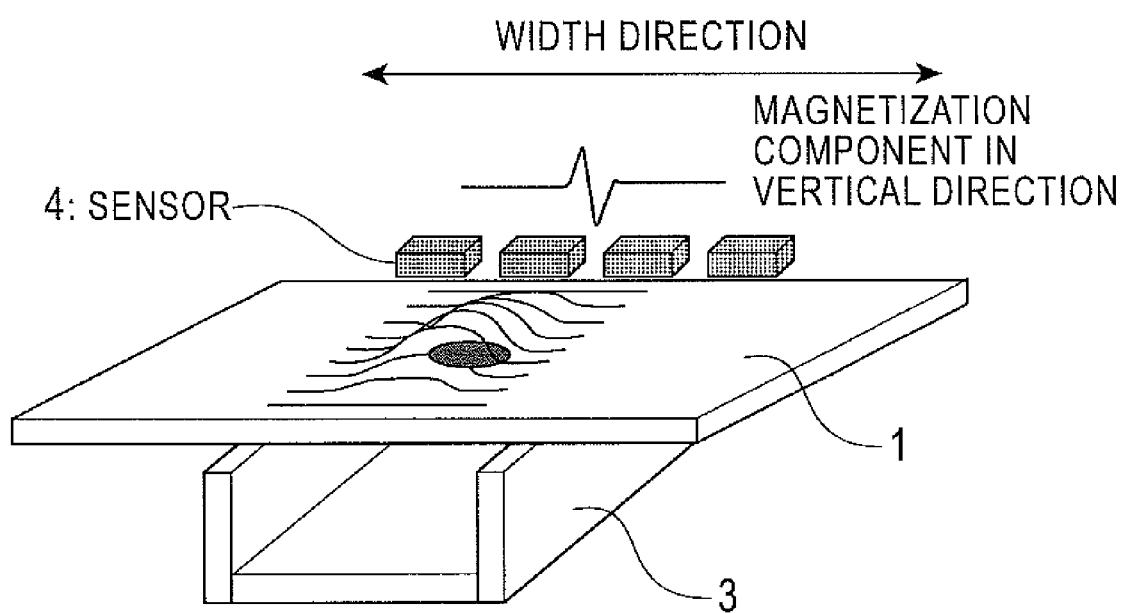
FIG. 8 is a schematic view of transverse magnetization.

In the measurement of the first example of FIG. 1, magnetization is performed in the longitudinal direction. However, as shown in FIG. 7, sensors detecting a magnetic field in the vertical direction may be arranged in the width direction, and magnetization may be performed in the width direction. In this case, the magnetic flux generated due to a defect has positive and negative distributions in the width direction (FIG. 8). When the periodicity is evaluated, the similarity between the two-dimensional areas is evaluated in Examples 1 and 2. However, by imparting characteristic positive and negative peaks to the defect signal by magnetization in the width direction, a probability of non-detection can be reduced to increase the periodicity evaluation accuracy even when data sampling as shown in FIG. 6 (C) is performed. This allows the periodicity evaluation even when extracted as described above.

Focusing on the fact that the defect signals arise over a plurality of magnetic sensors in the width direction, the computation is performed by selecting the two-dimensional area and the small area to evaluate the similarity in the two-dimensional area of the defect signals having two-dimensional characteristics, whereby the periodicity evaluation can be performed with higher accuracy.

ADDITIONAL EXAMPLES

Next, an application of the periodic defect detection device of the first example will be described.

Figure 9:
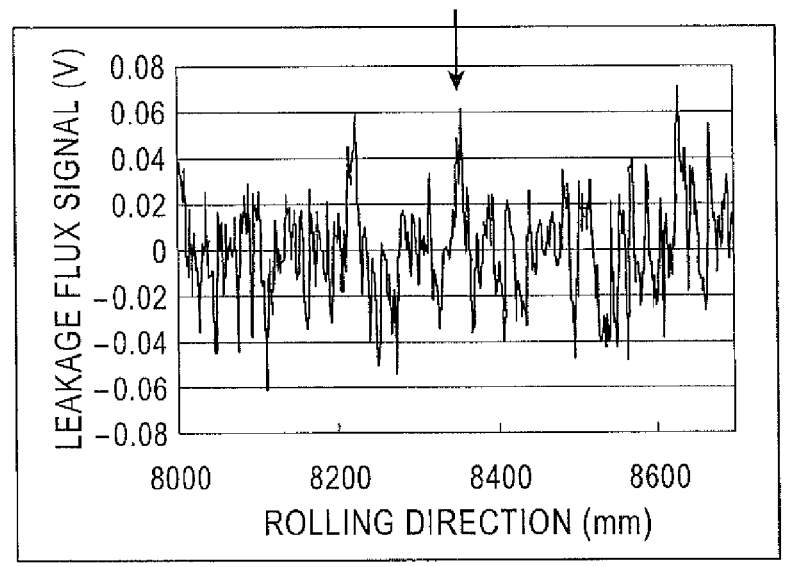
FIG. 9 shows an example of defect detection of a minor irregularity defect originating from a roll generated in a steel sheet production line.
Figure 10:
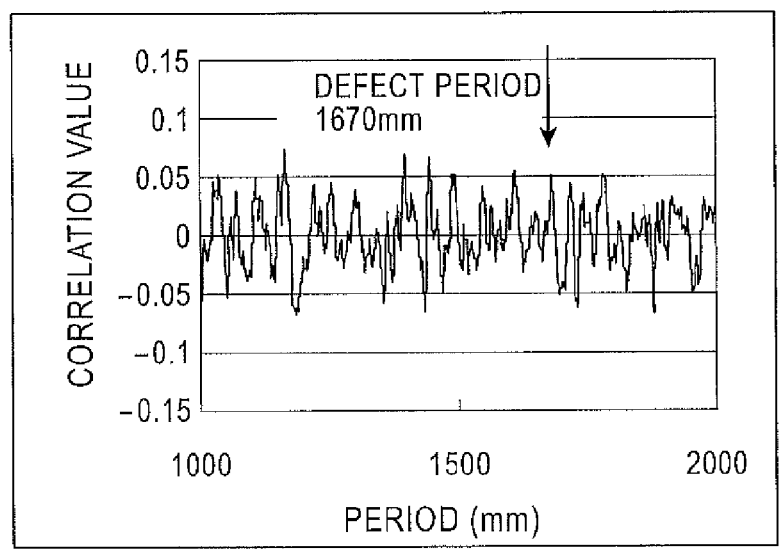
FIG. 10 is a view illustrating results of performing autocorrelation of a leakage flux signal of FIG. 9.

FIG. 9 shows an example of defect detection of a minor irregularity defect originating from a roll generated in a steel sheet production line. In FIG. 9, a defect position is indicated by the arrow. The defect signals have small differences compared with noise signals, and thus are hard to be automatically detected. FIG. 10 shows results of performing an autocorrelation operation as an example of subjecting the signal to a general signal processing. Even when the autocorrelation operation is performed using the original signals, a defect period (1670 mm) cannot be detected due to a small difference between the defect signal and the noise signal.

Figure 11:
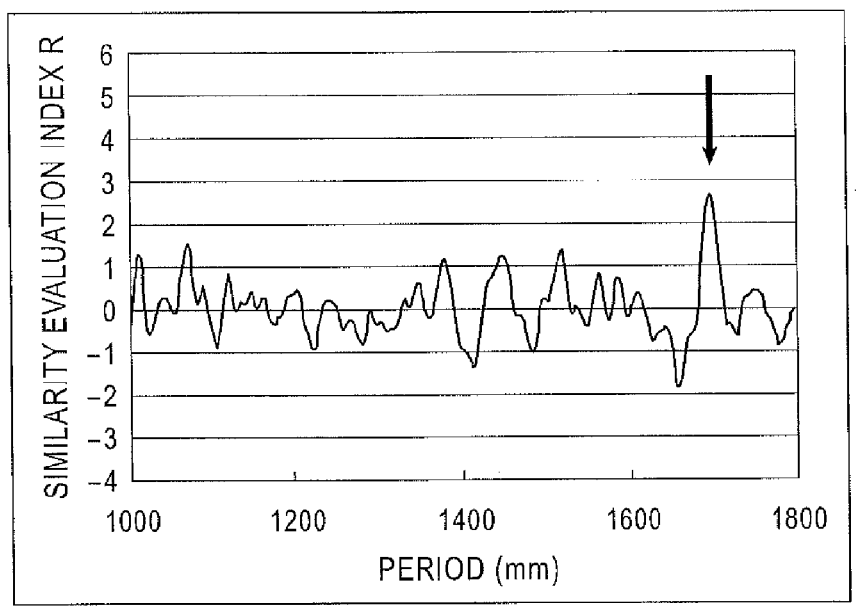
FIG. 11 is an example (No. 1) of a similarity evaluation index R obtained by a signal processing of the first example.
Figure 12:
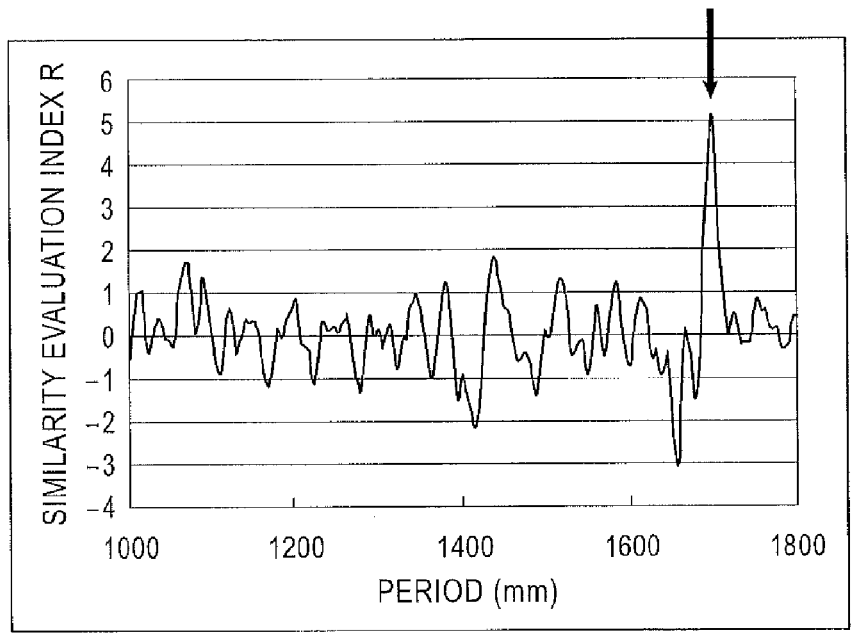
FIG. 12 is an example (No. 2) of a similarity evaluation index R obtained by the signal processing of the first example.

FIGS. 11 and 12 show results of performing the signal processing of the first example.

In FIG. 11, areas having a size of 8 mm in the width direction and 50 mm in the rolling direction are taken as a size of the first small area, and a correlation value of a pair of the areas is calculated to be used as a similarity evaluation index. In FIG. 11, the value of the similarity evaluation index R at the position (indicated by the arrow) of 1670 mm as the defect period is larger than that of another period. Therefore, in other words, it is recognized that the periodicity is strong (the value of the similarity evaluation index R is about 1.5 times larger than that of another period and the periodicity is about 1.5 times stronger than that of another period) and that the periodic defect exists. For example, in FIG. 11, a periodic defect can be discriminated by setting a threshold to R=1.5.

In FIG. 12, correlation values of 4 pairs of combination of areas whose sizes are the same as FIG. 6 are calculated and added to be used as the similarity evaluation index. In FIG. 12, it is clarified that the value of a similarity evaluation function R is much larger than that of another period and the periodicity is higher than that of another period (the value of the similarity evaluation function R is about 4 to 5 times larger than that of another period and the periodicity is about 4 to 5 times stronger than that of another period), and that the periodic defect exists. In FIG. 12, for example, when the threshold is set to R=2.5, the periodic defect discrimination accuracy can be further increased. Thus, the defect judgment can be performed by setting the differential threshold using the similarity evaluation index.

Thus, by determining and adding correlation values of 4 pairs of areas so as to evaluate the similarity, the defect periodicity can be more clearly detected. The periodicity can be determined even when the correlation value between two areas is used as the similarity index. The similarity evaluation result, i.e., reliability of the determined period, increases with an increase in the number of pairs of the areas whose correlation values are determined, however the calculation amount increases. From the relationship between the reliability of the results and the calculation amount, about 3 to 5 pairs are appropriate, and the 4 pairs as above are optimal.

In the example of Equation (3) above, the correlation values of the 4 pairs of areas are added to be used as the similarity evaluation index. Another method, such as multiplication or addition with a weight, may be used.

In the example above, two pairs of adjacent areas are selected as areas whose correlation values are determined. This is important for reducing influences of shift (deviation) in the width direction as much as possible in running of a target sample. In particular, since deviation in the width direction referred to as meandering arises during running in a steel line, effects by the calculation method are large. In the case of a target sample in which the deviation during running is small, 2 pairs of areas are not necessarily adjacent to one another. For example, by calculating correlations between the first reference position and each of a second area, a third area, a fourth area . . . , the calculation can be simplified.

In the example above, an example of a method using a correlation value is described as the similarity evaluation method. However, another similarity evaluation method, such as a differential integration processing, may be used.

Figure 13:
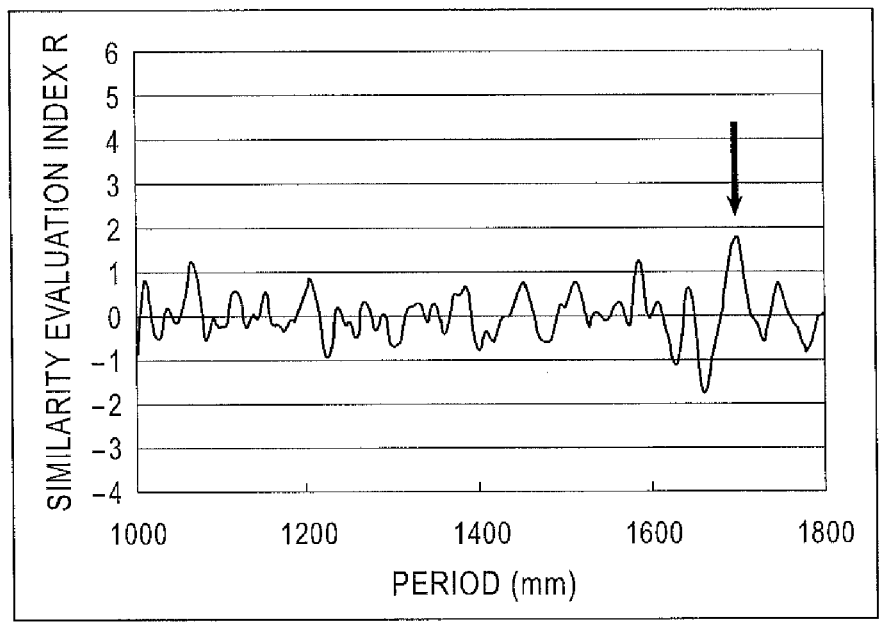
FIG. 13 is an example (No. 3) of a similarity evaluation index R obtained by the signal processing of the first example.
Figure 14:
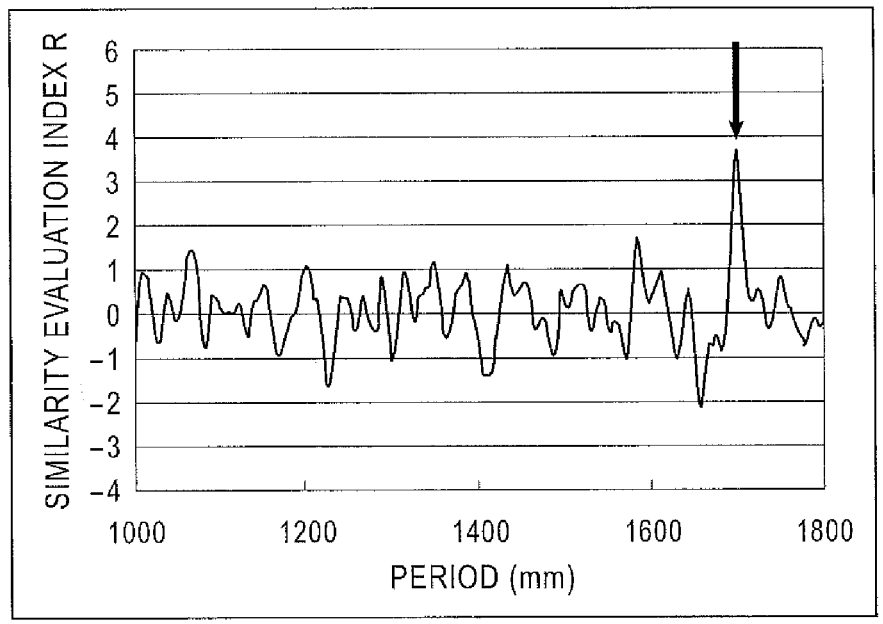
FIG. 14 is an example (No. 4) of a similarity evaluation index R obtained by the signal processing of the first example.

Next, FIGS. 13 and 14 show the results of changing the size of the first small area.

FIGS. 13 and 14 correspond to FIGS. 11 and 12, respectively, and calculation is performed under the same conditions except adjusting the size of the first small area to be 100 mm in the rolling direction. The measurement data show that the similarity evaluation value becomes worse when the size is adjusted to be 100 mm in the rolling direction, and the similarity evaluation value varies in accordance with the size of the area. This is because when the size of the first small area excessively increases compared with the defect size, the number of data of noise signals increases relative to the number of data of defect signals, which increases influences of the noise signals, resulting in poor S/N of the correlation value.

Figure 15A:
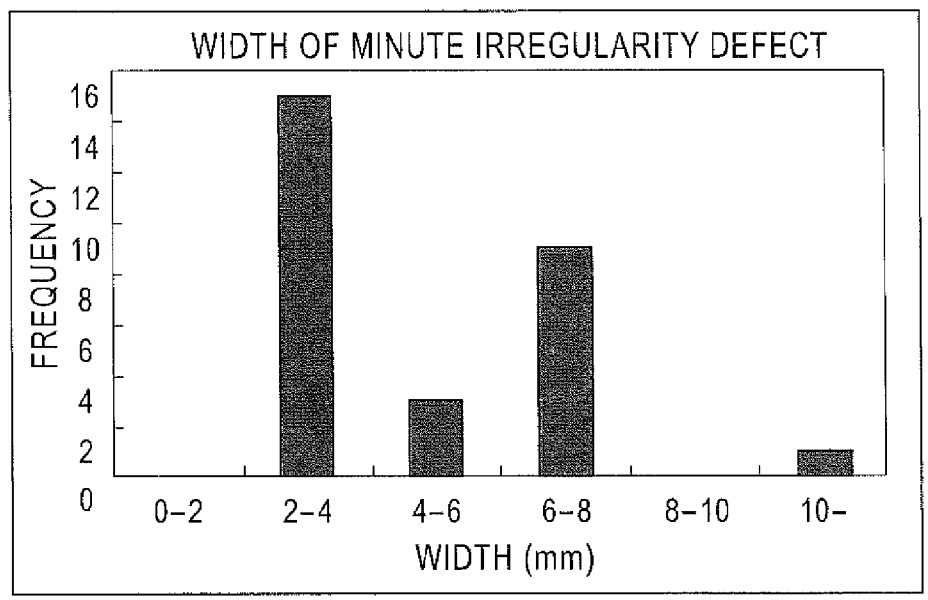
FIGS. 15A and 15B are views illustrating inspection results of a distribution of sizes of defects generated in a continuous annealing line.
Figure 15B:
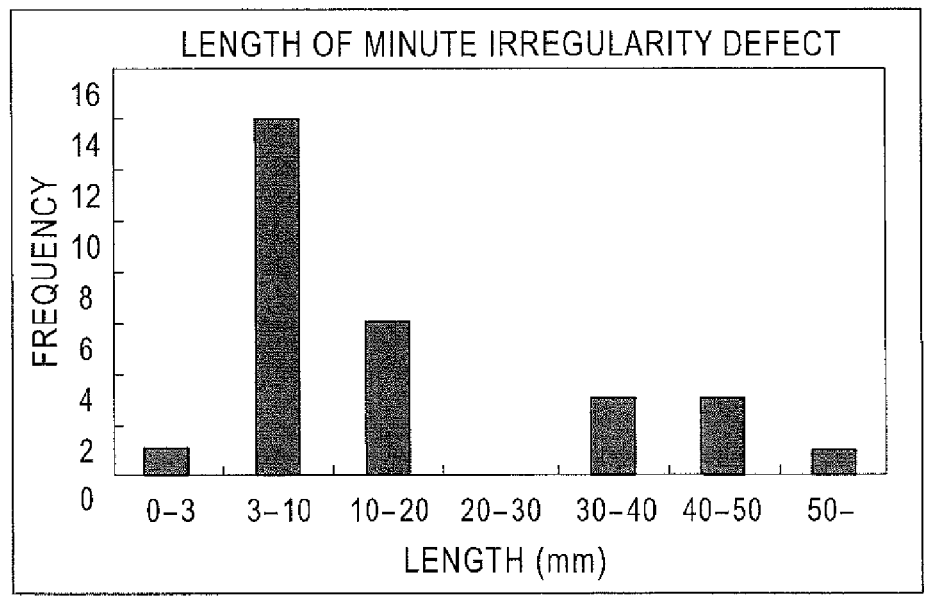

Among the defects originating from a roll in the steel line, a defect in the shape of irregularities of 5 μm or lower having a gently-sloping outline (radius of curvature of R≥10 mm) of the steel sheet surface roughness (Ra=0.5 to 2 μm) but an area of 10 mm$_2$ are referred to as minute irregularity defects and are particularly hard to be detected. We examined the distribution of sizes of defects generated in a continuous annealing line. As a result, we found that most of the defects had a length in the width direction of about 2 mm to about 8 mm and a length in the rolling direction of about 3 mm to 50 mm as shown in FIGS. 15A and 15B. When the minute irregularity defect is measured, it is appropriate that the size of the area whose correlation value is calculated is adjusted to the size of h=about 8 mm and l=about 50 mm which are equivalent to the maximum size of the defect. The similarity evaluation index R was calculated (Equation 3) while changing the widths (h) and lengths (l) of the window frames of areas (first and second small areas) whose correlation values are calculated relative to samples whose sizes were partially changed (the smallest defect size (3 mm in length×3 mm in width), the largest defect size (50 mm in length×10 mm in width)). Typical results are shown in FIGS. 16A and 16B.

Figure 16A:
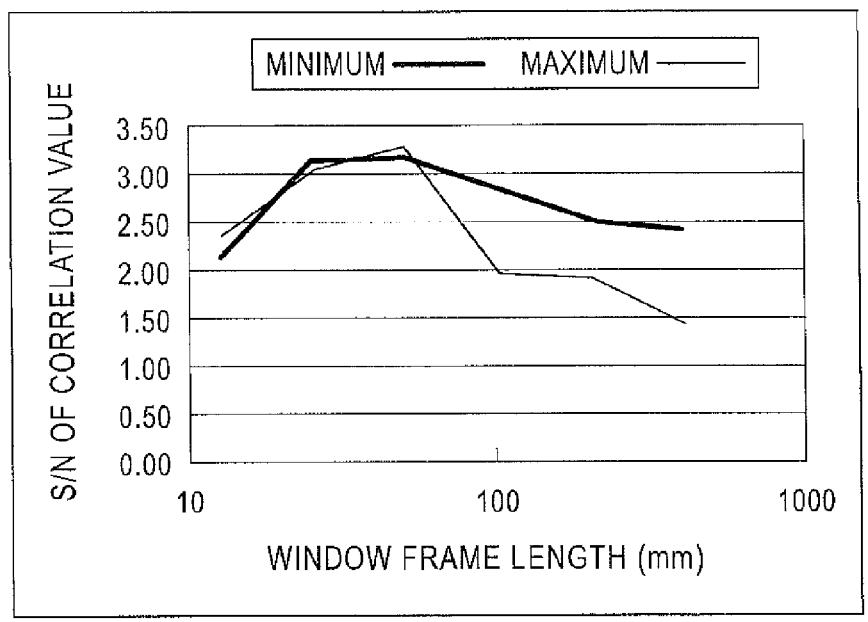
FIGS. 16A and 16B are views illustrating an example of S/N of the similarity evaluation index R obtained by changing the window length and the window width of the area with respect to the data of FIG. 15.
Figure 16B:
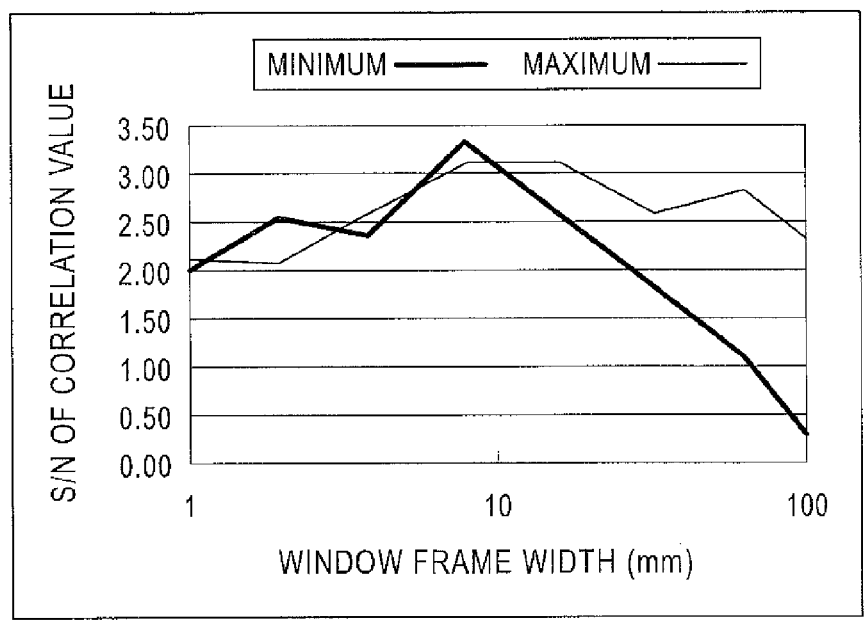

The axis of ordinate of each of FIGS. 16A and 16B represents a ratio (referred to as S/N) of the evaluation index values of the defect parts and the parts free from defects.

Based on the data, an applicable range of the small area is in the range of a length of 10 mm to 100 mm and a width of 1 mm to 30 mm (S/N≥2), an optimum range thereof is in the range of a length of 20 mm to 80 mm and a width of 2 mm to 20 mm (S/N≥25), and a more optimum range thereof is in the range of a length of 25 mm to 62 mm and a width of 7 mm to 11 mm (S/N≥3).

When the width and length of the window frame of the area is ¼ or more and twice or lower than the maximum width and length of an expected defect, respectively, the S/N become 2 or more, which can be applied to automatic defect detection. When the width and length of the window frame of the area are adjusted to be substantially the same as the maximum width and length of an expected defect, the S/N becomes 3 or more, which is found to be optimal.

Figure 17:
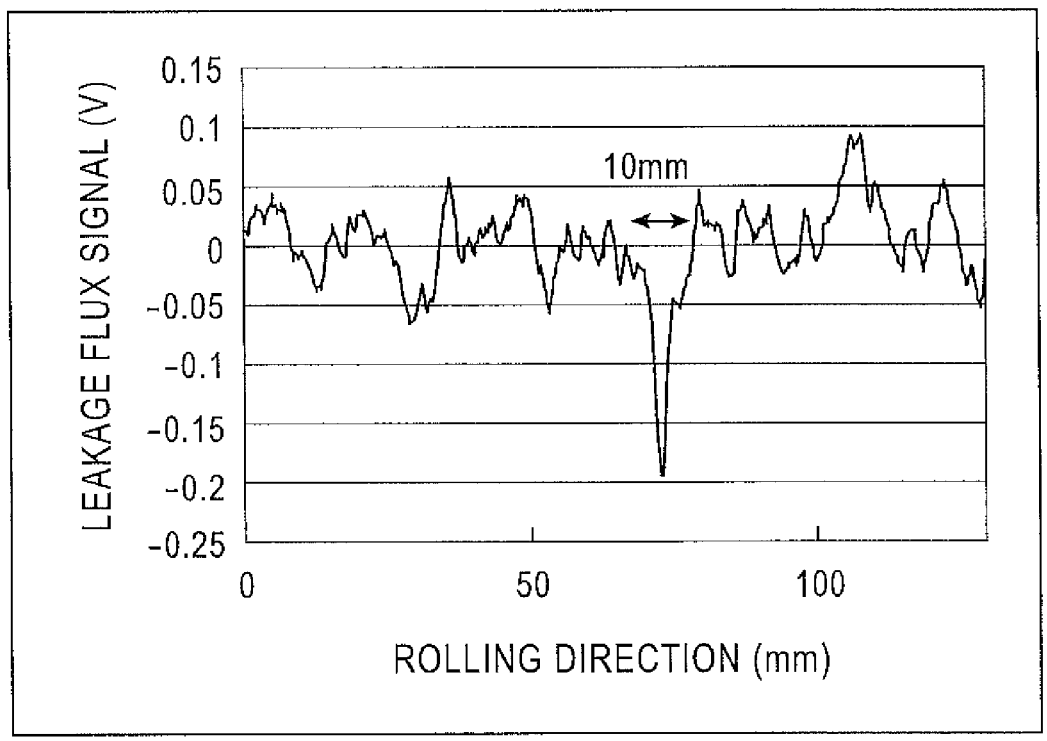
FIG. 17 is a view illustrating an example of a measurement signal of the first example.
Figure 18:
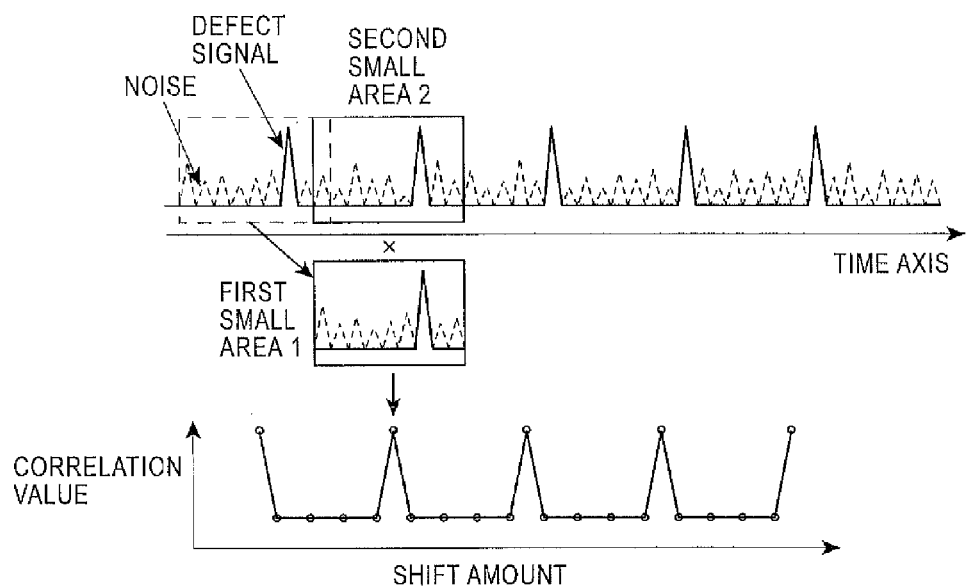
FIG. 18 is an explanatory view illustrating a former periodic defect detection method.
Figure 19:
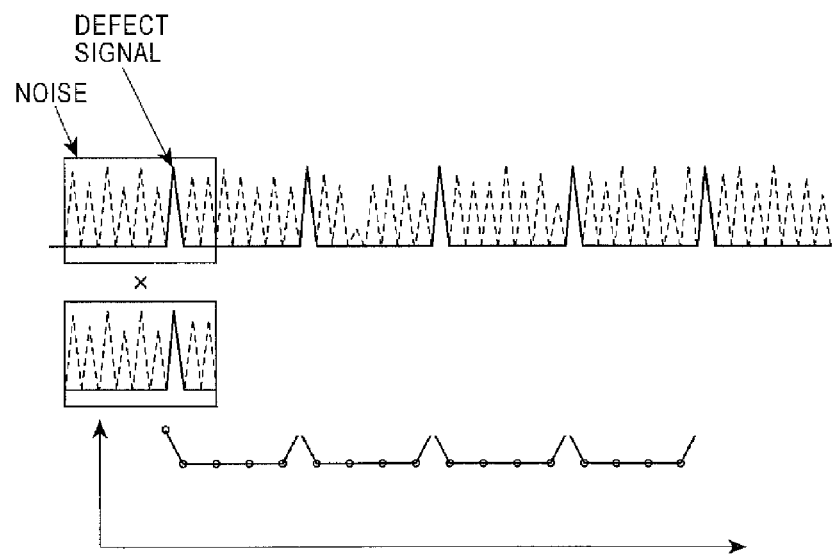
FIG. 19 is an explanatory view illustrating a former periodic defect detection method.

Since the measurement signal by the magnetic sensor of this example has an about 10 mm spread in the rolling direction as shown in FIG. 17, a large difference does not appear in the optimum range compared with the relative ratio of the defect size in FIG. 9. The lower limit of the optimum range may be the maximum defect size. However, the upper limit of the optimum range is considered to be based on the spread of the measurement signal. Thus, when the optimum range is indicated in another way, the optimum range is equal to or higher than ¼ of the maximum defect size and is equal to or lower than 10 times the smallest spread of the signal, more preferably equal to or higher than ⅔ of the maximum defect size and is equal to or lower than 8 times the smallest spread of the signal, and still more preferably equal to or higher than ½ of the maximum defect size and is equal to or lower than 6 times the smallest spread of the signal.

In the examples above, leakage-flux defect detection has been described. The leakage-flux defect detection is not necessarily used and another method may be used insofar as the method evaluates the properties of a target sample. Another defect detection method, such as a surface defect meter using a usual camera, a sensor using infrared light, a thermography, an ultrasonic sensor, or an eddy current sensor, may be used.

In the technique of JP 2006-105791, optical defect inspection is performed, and the fact that the base pattern as noise of the part free from defects of the obtained signal has the same periodicity as the circumferential length of a final reduction roll is utilized. However, in the leakage-flux defect detection, the noise of the part free from defects are influenced by not only surface irregularities but distortion produced by subtle conditions, such as rolling reduction during rolling or temperature unevenness. Thus, in the leakage-flux defect detection, the noise of the part free from defects does not necessarily have the same period as the final reduction roll. Therefore, effects obtained by evaluating similarity for each area surrounding the defect part are large in the leakage-flux defect detection.

As a leakage flux sensor, a magnetic sensor, such as a hall element, a coil, a magnetic resistance element, or SQUID, can be used. Although a plurality of sensors are arranged in the width direction, a method in which one or a plurality of sensors are traversed may be used. The defect detection is performed over the entire width, a method in which the defect detection is performed in a partial area in the width direction may be used. In particular, in the case of continuous periodic defects, a method may be used in which the defect detection is performed in a partial area in the width direction to a certain length, and then the defect detection is repeatedly performed while changing the position in the width direction.

The magnetizer 3 is provided so that the magnetic flux flows in the width direction of the steel sheet. Here, a pair of the magnetizer and the magnetic sensor is faced with each other across the steel sheet 1, but may be provided on the same side.

What is claimed is:

1. An apparatus for detecting periodic defects comprising:
    a sensor that obtains signals to evaluate properties of an area having a length longer than an expected defect period on a target sample;
    a small area selector that separates a plurality of small areas, wherein a length of each small area is shorter than the length of the area and the length of each small area is between the range of ¼ or more and twice or less than the maximum length of an expected defect, so that all distance intervals adjacent to one another are equal in a periodic defect arrangement direction to determine positions of the plurality of small areas, and selecting signals corresponding to the positions of the plurality of small areas from outputs from the sensor;
    an evaluation index calculator that calculates a similarity evaluation index between signal patterns among a plurality of signals selected by the small area selector;
    a set value changer that changes the positions of the small areas and the distance interval, and repeating computational processings of the small area selector and the evaluation index calculator;
    a period judgment device that judges the distance interval as a period when the evaluation index is higher than a value set beforehand; and
    a defect judgment means that judges the existence of a periodic defect in the small area on the basis of signals in the small area in which the periodicity judging is conducted,
    wherein the small area selector comprises:
    a first small area selector that determines one position of a small area whose length is shorter than the length of the area to define the small area as a first small area, and selecting a signal corresponding to the position of the first small area from the sensor output; and
    a second small area selector that disposes a plurality of second small areas having the same size as the first small area in a periodic defect arrangement direction on the basis of the position of the first small area while separating the second small areas so that all distance intervals are equal, and selecting signals corresponding to positions of the plurality of second small areas from the sensor output, and
    the set value changer changes the position of the first small area and the distance interval, and repeats computational processings of the small area selector and the evaluation index calculator; and
    wherein the sensor is a magnetic sensor that magnetizes a target sample formed of a magnetic metal component, and obtains a leakage flux signal.

2. The apparatus according to claim 1, wherein the length of the small area is substantially the same as the length of an expected largest defect.

3. The apparatus according to claim 1, wherein the evaluation index calculator calculates a value for evaluating similarity for each small area, and combines the values to determine the evaluation index.

4. The apparatus according to claim 1, wherein the evaluation index calculator calculates a value for evaluating similarity for each small area, and adds the values to obtain the evaluation index.

5. The apparatus according to claim 1, wherein the value for evaluating similarity for each small area is a correlation value between the small areas.

6. A method for detecting periodic defects comprising:
    (a) a signal inputting step of obtaining sensor outputs for evaluating properties of an area whose length is longer than that of an expected defect period on a target sample;
    (b) a small area selecting step of separating a plurality of small areas, wherein a length of each small area is shorter than the length of the area and the length of each small area is between the range of ¼ or more and twice or less than the maximum length of an expected defect, so that all distance intervals adjacent to one another are equal in a periodic defect arrangement direction to determine positions of the plurality of small areas, and selecting signals corresponding to the positions of the plurality of small areas from the sensor outputs;
    (c) an evaluation index calculation step of calculating a similarity evaluation index between signal patterns among a plurality of signals selected in the small area selecting step, using a processor;
    (d) a set value changing step of changing positions of the small areas and the distance interval, and repeating (b) and (c) above;
    (e) a period judging step of judging the distance interval to be a period when the evaluation index determined in (c) above is higher than a value set beforehand; and
    (f) a defect judging step of judging the existence of a periodic defect on the basis of signals in which the periodicity judging in (c) above is conducted,
    wherein the small area selecting step determines one position of a small area whose length is shorter than the length of the area to define the small area as a first small area, disposes a plurality of second small areas having the same size as the first small area in a periodic defect arrangement direction on the basis of the position of the first small area while separating the second small areas so that all distance intervals are equal, and selects signals corresponding to the position of the first small area and the positions of the plurality of second small areas from the sensor outputs, and
    the set point changing step repeats (b) and (c) above while changing the position of the first small area and the distance interval, and
    wherein the sensor is a magnetic sensor that magnetizes a target sample formed of a magnetic metal component, and obtains a leakage flux signal.

7. The apparatus for detecting periodic defect according to claim 1, wherein the defect judging device judges the signal, which is judged as a defect candidate by the periodic judging device, to determine whether the defect candidate is a periodic defect on the basis of the signal strength, length in the width direction, length in the rolling direction, and defect shape of the defect candidate.

* * * * *